United States Patent

Nakamura et al.

[11] Patent Number: 5,880,109
[45] Date of Patent: *Mar. 9, 1999

[54] METHOD OF ACCELERATING INTESTINAL ABSORPTION OF CALCIUM IN MAMMALS

[75] Inventors: Satoshi Nakamura; Takeya Yoshioka; Shingo Hamada; Ikuo Kimura, all of Tokyo, Japan

[73] Assignee: Nippon Suisan Kaisha, Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 811,292

[22] Filed: Mar. 4, 1997

Related U.S. Application Data

[63] Continuation of Ser. No. 366,115, Dec. 29, 1994, abandoned.

[30] Foreign Application Priority Data

Dec. 29, 1993 [JP] Japan ................................. 5-355022

[51] Int. Cl.⁶ ...................................................... A61K 31/73
[52] U.S. Cl. ................................................ 514/55; 536/20
[58] Field of Search ................................. 536/20; 514/55

[56] References Cited

U.S. PATENT DOCUMENTS

| 4,833,237 | 5/1989 | Kawamura et al. | 536/20 |
| 4,971,956 | 11/1990 | Suzuki et al. | 514/55 |
| 5,244,469 | 9/1993 | Shimoyama et al. | 8/438 |
| 5,498,533 | 3/1996 | Poovaiah et al. | 435/172.3 |

FOREIGN PATENT DOCUMENTS 0592964  4/1994  European Pat. Off. .

OTHER PUBLICATIONS

Kauss *J. Cell. Sci.* 1985, Suppl. 2, 89–103.
Waldmann et al. *Planta* 1988, 173, 88–95.
Lee et al. *Korean Biochem. J.* 1992, 25 (5), 387–392.
Kawamura et al. *Ind. Eng. Chem. Res.* 1993, 32, 386–391.
Gordon et al. In "Unconventional Sources of Dietary Fiber", *ACS Symposium Series*, 1983, 214, 155–184.

*Primary Examiner*—Kathleen K. Fonda
*Attorney, Agent, or Firm*—Sughrue, Mion, Zinn, Macpeak & Seas, PLLC

[57] ABSTRACT

A composition for accelerating calcium absorption containing water-soluble chitosan as an active ingredient is disclosed. The composition is useful as an additive for foods, feed, and pharmaceutical preparations.

4 Claims, 1 Drawing Sheet

_(Continuation of application Ser. No. 08/366,115, filed Dec. 29, 1994, now abandoned.)_

METHOD OF ACCELERATING INTESTINAL ABSORPTION OF CALCIUM IN MAMMALS

This is a continuation of application Ser. No. 08/366,115, filed Dec. 29, 1994, now abandoned.

FIELD OF THE INVENTION

This invention relates to a composition for accelerating calcium absorption containing water-soluble chitosan and a method of accelerating calcium absorption. The calcium absorption accelerating composition of the present invention is used in foods, feed, and pharmaceutical preparations as an additive for calcium absorption acceleration. The present invention provides foods, feed or pharmaceutical preparations containing water-soluble chitosan as a calcium absorption accelerating additive.

BACKGROUND OF THE INVENTION

According to the results of the nation-wide survey of nutrition made by the Ministry of Public Welfare, Japan in 1991, a Japanese calcium intake is 540 mg/day in average, which is considerably lower than the recommended calcium allowance specified by the same ministry, i.e., 600 mg/day. Shortage of calcium intake recently turned out to cause serious diseases, such as osteoporosis, hypertension, and large bowel cancer. In particular, osteoporosis easily causes fractures, and it is very likely that an aged patient suffering from a fracture of femoral neck or a compression fracture of the lumber vertebra gets bed-ridden. In fact, the second cause of making the aged become the bed-ridden is a fracture. It is said that the number of patients with osteoporosis has reached about 5,000,000 and will be increasing steadily to pose a serious social problem in an aging society ahead.

What is wanted to ameliorate the present situation is to increase a calcium intake so as to always supply sufficient amount of calcium to the body. However, an average Japanese' calcium intake per day has never exceed the recommended allowance (600 mg) according to the survey taken by the Ministry of Public Welfare every year, revealing difficulty to assure a sufficient level of a calcium intake through daily food. While calcium-containing pharmaceuticals and calcium-enriched foods are available, they are inferior in palatability and difficult to take habitually.

Under these circumstances, it is important, the inventors thought, that orally taken calcium be absorbed efficiently through the intestine, the absorption site for calcium. It is considered that the ratio of calcium absorbed through the intestine and utilized for maintenance of a living body in the total calcium orally taken is about 20 to 50%, while somewhat varying depending on the origin of calcium, so that the most of orally taken calcium is excreted without being absorbed. Therefore, an increase in percent absorption of calcium in the intestinal tract would fulfill the calcium requirement without forcing unnatural calcium intake.

Vitamin D and lactose are commonly used as a component which accelerates calcium absorption in the field of foods and pharmaceuticals. Because vitamin D is biosynthesized, administration of vitamin D is not expected to act for acceleration of calcium absorption in those who can synthesize sufficient vitamin D in their own body. Lactose is not favorable to those who suffer from lactose intolerance because of side effects, such as diarrhea.

Additionally, peptide of bone origin (see JP-A-4-16165, the term "JP-A" as used herein means an "unexamined published Japanese patent application") and a composition mainly comprising butyric acid (see JP-A-4-108360) have been proposed as a component for calcium absorption acceleration. However, neither of them has been put to practical use due to involvement of problems in production and use.

It is known that oral intake of calcium in combination with other food components results in a slightly increased calcium absorption as compared with single calcium intake. This phenomenon is accounted for as follows. Food entering the stomach stimulates secretion of gastric juice to lower the gastric pH value so that calcium, which is generally water insoluble, is dissolved by the action of the acid and thereby becomes ready to be absorbed. However, in what manner a food component takes part in absorption of calcium through the intestine has not been studied intensively.

SUMMARY OF THE INVENTION

An object of the present invention is to provide a calcium absorption accelerating composition which is effective for accelerating calcium absorption through the intestine.

Another object of the present invention is to provide a method of accelerating calcium absorption which comprises adding calcium absorption accelerating component to foods, feed, and pharmaceutical preparations.

The inventors of the present invention conducted investigations into the influences of various components present in food on calcium absorption and found, as a result, that water-soluble chitosan has an effect of accelerating calcium absorption in the intestinal tract.

The present invention relates to a calcium absorption accelerating composition containing water-soluble chitosan as an active ingredient.

The composition of the present invention is used as a calcium absorption accelerating additive for foods, feed and pharmaceutical preparations.

DETAILED DESCRIPTION OF THE INVENTION

Figure 1:
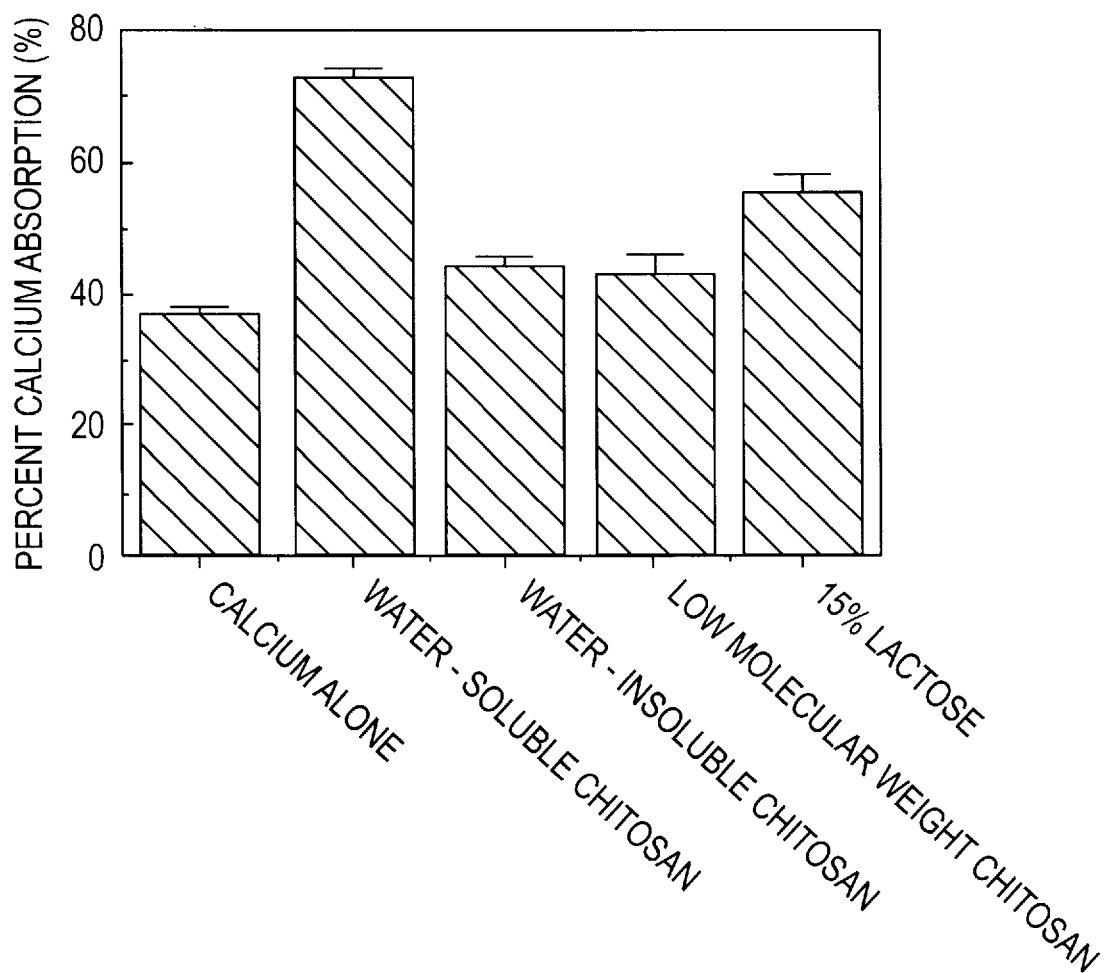
FIG. 1 is a graph of percent calcium absorption, showing the influences of various components on calcium absorption.

The calcium absorption accelerating composition (hereinafter sometimes referred simply to as "the composition") of the present invention may further contain a calcium salt. In this case, the composition contains water-soluble chitosan and a calcium salt both as active ingredients.

Chitosan generally means a partial or complete deacetylation product of chitin [poly(N-acetylglucosamine)]. Chitin is a structural polysaccharide present in shells of Crustacea and cuttlebones. For example, carapaces of crabs, such as Chionoecetes, which are by-produced in large quantity in processing of the crab meat contain about 15% by weight of chitin. Therefore, chitin is a biomaterial the effective utilization of which has been expected. Both chitin and chitosan, when orally taken, serve as dietary fiber in the intestine and are, needless to say, safe to the human body.

Water-soluble chitosan which can be used in the present invention is obtained by, for example, reducing the molecular weight of chitosan, preferably to 10,000 or less, for solubilization. Known techniques for reducing the molecular weight of chitosan to make it water-soluble include a method of using a nitrite (see JP-A-61-184002), a method of using a peracid or a mineral acid, and a method of using an enzyme. In addition to the above-described degradation products of chitosan, water-soluble chitosan obtained by other methods, such as partial deacetylation of chitosan or addition of an appropriate acid, can also be used in the present invention. Specific examples of the water-soluble chitosan include Flonac S (trade name of the products manufactured by Kyowa Tecnos Co., Ltd.) having a weight average molecular weight of 2,540 determined by the gel permeation chromatography (GPC) method (HPLC) and Flonac S having a weight average molecular weight of 5,000 determined by the GPC method (HPLC) [hereinafter referred to as, for example, Flonac S (M.W. 2,540)]. The water-soluble chitosan has a molecular weight of preferably 5,000 or less, more preferably 1,000 to 2,500.

The water-soluble chitosan of the invention may be in the form of liquid or powder (e.g., freeze-dried or spray-dried product).

The composition of the present invention contains water-soluble chitosan in an amount effective to accelerate calcium absorption, specifically 0.001 to 10% by weight.

Of various saccharides, galacto-oligosaccharide (JP-A-4-134031), Theanderose (JP-A-4-360664), and fructo-oligosaccharide (Journal of Japanese Society of Nutrition and Food Science, No. 46, p. 123 (1993)) are known to be effective in calcium absorption acceleration. It is utterly unknown that water-soluble chitosan has an effect in calcium absorption acceleration.

As a calcium salt to be used in the composition of the invention, mention may be made of synthetic products, such as calcium carbonate or calcium chloride and natural products, such as bovine bones or eggshell. The calcium salt is contained in the composition in an amount effective to accelerate calcium absorption, preferably 0.01 to 30% by weight.

The water-soluble chitosan can also be used in combination with known calcium absorption accelerating components, such as vitamin D, lactose, casein phosphopeptide or arginine.

The composition of the invention may further contain food additives or pharmaceutically acceptable carrier commonly used, such as antioxidant, viscosity-increasing agent, stabilizer, emulsifier, preservative, or quality-improving agent.

The method of accelerating calcium absorption of the present invention comprises adding the water-soluble chitosan to foods, feed or pharmaceutical preparations in an amount effective to accelerate calcium absorption. The above-described calcium salt may be added in combination with the water-soluble chitosan in an amount effective to accelerate calcium absorption.

Foods to which the composition of the present invention can be added include beverages, snacks, cereals, noodles, paste, and tablets. For use in feed, the composition of the present invention is compounded into general feed for animals. For use in pharmaceutical preparations, the composition of the present invention can be formulated together with other ingredients into tablets, granules, solutions, and the like.

These foods, feed and pharmaceutical preparations are usually orally given to the subjects. The preparations containing the composition may be given directly to the digestive tract when formulated into a suitable dosage form.

The present invention will now be illustrated in greater detail by way of Examples, but it should be understood that the present invention is not to be construed as being limited thereto. All the percents and parts are by weight unless otherwise indicated.

EXAMPLE 1

The effect of water-soluble chitosan on acceleration of calcium absorption was examined by the following test.

1) Preparation of Samples:

Water-soluble chitosan [Flonac S (M.W. 2,540)] was dissolved in water in a concentration of 0.5%, and calcium chloride was dissolved therein to a calcium concentration of 150 mM. The solution was adjusted to pH 6.5 with hydrochloric acid or sodium hydroxide to prepare a test sample.

As comparative samples, a 150 mM calcium chloride aqueous solution, a 150 mM calcium chloride aqueous solution containing 15% of lactose having a calcium absorption accelerating effect, a 0.5% aqueous suspension of insoluble chitosan [Flonac C (M.W. 50,000 determined by the GPC method (limiting viscosity method))], and a 0.5% aqueous suspension of chitin were prepared.

2) Test Animals:

Four-week-old SD male rats (Nippon Charles River) were divided into five groups each consisting of six animals. The rats were fasted overnight.

3) Calcium Absorption Test:

Calcium absorption was examined by an intestinal tract double ligature test in rats. That is, rats were anesthetized with Nembutal and subjected to laparotomy. The duodenum was ligated at two positions to make a 4 cm long sausage-like loop. Each of the sample solution (0.3 ml) was injected into the loop of the duodenum. After the rat was left to stand for 1 hour while warming the body at about 37° C. so that the body temperature might not drop, the loop part of the duodenum was cut out, and the calcium remaining therein was measured with atomic absorption analyzer. The percent absorption of calcium (Ca) was calculated according to the following equation:

$$\text{Percent Ca Absorption (\%)} = \frac{(\text{Amount of Ca in Sample Solution} - \text{Amount of Ca Remaining in Duodenum})}{(\text{Amount of Ca in Sample Solution})} \times 100$$

4) Test Results:

The results are shown in FIG. 1. The water-soluble chitosan group showed significantly higher calcium absorption than the calcium group and also higher than the group of lactose which is recognized to accelerate calcium absorption. The insoluble chitosan-containing solution and the chitin-containing solution used for comparison gave no influence on calcium absorption. It is seen that the above-mentioned increase in calcium absorption is characteristic of the water-soluble chitosan.

EXAMPLE 2

The components listed in Table 1 were mixed to have the composition as shown in Table 1 and sterilized by heating at 90° C. for 40 minutes to obtain a calcium-enriched beverages containing a calcium absorption accelerating component.

TABLE 1

| Components | Part by weight |
| --- | --- |
| Valencia orange juice | 85 |
| Sugar | 11 |
| Citric acid | 2 |
| Orange flavor | 1 |
| Spice | 0.4 |
| Calcium chloride | 0.1 |
| Water-soluble chitosan | 0.5 |

EXAMPLE 3

The components listed in Table 2 were mixed and emulsified so as to have the composition as shown in Table 2 to prepare a nutritious drink excellent in calcium absorption.

TABLE 2

| Components | Part by weight |
| --- | --- |
| Casein decomposition product | 35 |
| Dextrin | 153 |
| Palm oil | 32.5 |
| Soybean oil | 57.8 |
| Sodium chloride | 1.0 |
| Potassium chloride | 5.4 |
| Magnesium chloride | 2.5 |
| Calcium glycerophosphate | 3.5 |
| Ferric chloride | 0.029 |
| Manganese sulfate | 0.022 |
| Zinc sulfate | 0.012 |
| Copper sulfate | 0.011 |
| Vitamin A palmitate | 0.030 |
| Cholecalciferol | 0.00013 |
| Tocopherol | 0.4 |
| Vitamin $B_1$ nitrate | 0.0009 |
| Riboflavin | 0.0013 |
| Vitamin $B_6$ | 0.002 |
| Sodium ascorbate | 0.056 |
| Nicotinic acid amide | 0.015 |
| Calcium pantothenate | 0.0076 |
| Folic acid | 0.0002 |
| Cyanocobalamin | 0.0002 |
| Emulsifying agent | 10 |
| Water | 1334 |
| Water-soluble chitosan | 1 |

EXAMPLE 4

Calcium absorption accelerating component-added lemon jelly was prepared as follows. In 475 g of warm water were dissolved 15 g of gelatin powder and 120 g of sugar. Then, 20 g of lemon juice, 10 g of lemon peel, 3 g of white curacau, 3 g of calcium chloride, and 1 g of water-soluble chitosan were added thereto, followed by stirring. The mixture was put into a container and set in a mold in a refrigerator for 3 hours to obtain calcium absorption accelerating additive-added lemon jelly.

EXAMPLE 5

Calcium-enriched fish sausage containing a calcium absorption accelerating component was prepared as follows. Mashed meat of Theragra (1150 g) was salted with 35 g of sodium chloride and 430 g of ice-water, 30 g of sugar, 85 g of potato starch, 20 g of powdered skim milk, 20 g of seasonings, 260 g of soybean oil, 2 g of food coloring, 5 g of water-soluble chitosan and 5 g of calcium carbonate were further added thereto. The resulting mixture was mashed with a masher and the mixed paste was stuffed into casings. Each casing stuffed with the paste was sealed and put into a retort to sterilize at 118° C. for 20 minutes. Thus, calcium absorption accelerating component-added and calcium-enriched fish sausage was obtained.

As described above, the present invention provides a calcium absorption accelerating composition containing water-soluble chitosan which can be used as a calcium absorption accelerating additive in foods, feed and pharmaceutical preparations. That is, the present invention provides a calcium absorption accelerating composition which can be given to anyone, from infants to older persons short of calcium intake, and mammals to efficiently increase a calcium absorption through the intestinal tract and to promote healthy physiological activity.

While the invention has been described in detail and with reference to specific examples thereof, it will be apparent to one skilled in the art that various changes and modifications can be made therein without departing from the spirit and scope thereof.

What is claimed is:

1. A method for accelerating intestinal absorption of calcium in a mammal in need of accelerated calcium absorption comprising orally administering a food, beverage, feed or pharmaceutical preparation to said mammal, wherein said food, beverage, feed or pharmaceutical preparation comprises water-soluble chitosan in an amount effective to accelerate intestinal absorption of calcium of said mammal.

2. The method as claimed in claim 1, wherein said water-soluble chitosan has a molecular weight of 10,000 or less.

3. The method as claimed in claim 1, wherein said food, beverage, feed or pharmaceutical preparation additionally comprise a calcium salt.

4. The method as claimed in claim 3, wherein said calcium salt is in a form selected from the group consisting of calcium carbonate and calcium chloride.

* * * * *